United States Patent
Musset et al.

(10) Patent No.: US 12,152,971 B2
(45) Date of Patent: Nov. 26, 2024

(54) DEVICE FOR PRODUCING GASEOUS $CO_2$ FROM CARBONATES FOR ISOTOPIC ANALYSIS ($\delta^{13}C$ AND $\delta^{18}O$) IN SITU, AND ASSOCIATED METHOD

(71) Applicants: UNIVERSITE DE BOURGOGNE, Dijon (FR); CENTRE NATIONAL DE LA RECHERCHE SCIENTIFIQUE, Paris (FR); UNIVERSITE DE BRETAGNE OCCIDENTALE, Brest (FR)

(72) Inventors: Olivier Musset, Dijon (FR); Christophe Thomazo, Dijon (FR); Pierre Sans Jofre, Charenton-le-pont (FR); Théophile Cocquerez, Longecourt-en-Plaine (FR); Stefan Lalonde, Brest (FR)

(73) Assignees: UNIVERSITE DE BOURGOGNE, Dijon (FR); CENTRE NATIONAL DE LA RECHERCHE SCIENTIFIQUE, Paris (FR); UNIVERSITE DE BRETAGNE OCCIDENTALE, Brest (FR)

( * ) Notice: Subject to any disclaimer, the term of this patent is extended or adjusted under 35 U.S.C. 154(b) by 514 days.

(21) Appl. No.: 17/597,175

(22) PCT Filed: Jun. 30, 2020

(86) PCT No.: PCT/EP2020/068346
§ 371 (c)(1),
(2) Date: Dec. 28, 2021

(87) PCT Pub. No.: WO2021/001344
PCT Pub. Date: Jan. 7, 2021

(65) Prior Publication Data
US 2022/0307953 A1 Sep. 29, 2022

(30) Foreign Application Priority Data

Jul. 1, 2019 (FR) .................................. 1907289

(51) Int. Cl.
*G01N 1/44* (2006.01)
*G01N 1/02* (2006.01)
(Continued)

(52) U.S. Cl.
CPC ................ *G01N 1/44* (2013.01); *G01N 1/02* (2013.01); *G01N 33/24* (2013.01); *G01N 2001/028* (2013.01); *G01N 2001/045* (2013.01)

(58) Field of Classification Search
CPC ....... G01N 2001/028; G01N 2001/045; G01N 33/24; G01N 1/44; G01N 1/02
(Continued)

(56) References Cited

U.S. PATENT DOCUMENTS

| 5,656,186 A * | 8/1997 | Mourou | B23K 26/53 |
| | | | 219/121.69 |
| 8,642,918 B2 * | 2/2014 | Unrath | B23K 26/705 |
| | | | 359/239 |

(Continued)

FOREIGN PATENT DOCUMENTS

| CN | 104458979 A | 3/2015 |
| CN | 105527274 A | 4/2016 |

(Continued)

OTHER PUBLICATIONS

French Search Report received for Application No. 1907289, dated Mar. 3, 2020.

(Continued)

*Primary Examiner* — Nathaniel T Woodward
(74) *Attorney, Agent, or Firm* — Greer, Burns & Crain, Ltd (57) ABSTRACT

A device for preparing a gaseous sample obtained from a solid sample. The device includes a laser source arranged to emit a laser beam which is capable of generating calcination and/or combustion of a portion of the solid sample, a collector arranged to collect a gaseous sample of a gas emitted during the calcination and/or combustion of the portion of the solid sample; the laser beam has an irradiance less than 5 MW/cm$^2$ in a given impact zone on a surface of the sample, and including an optical fibre for propagating the laser beam between the laser source and the given impact zone on the surface of the sample.

19 Claims, 5 Drawing Sheets

(51) Int. Cl.
  *G01N 33/24* (2006.01)
  *G01N 1/04* (2006.01)
(58) Field of Classification Search
  USPC .......................................................... 73/19.12
  See application file for complete search history.

(56) References Cited

U.S. PATENT DOCUMENTS

| | | | |
|---|---|---|---|
| 10,222,337 B1* | 3/2019 | Yoo | H01J 49/105 |
| 2002/0163735 A1* | 11/2002 | Detlef | G01N 21/718 |
| | | | 359/639 |
| 2012/0206722 A1* | 8/2012 | Grigoropoulos | G01N 21/718 |
| | | | 356/318 |

FOREIGN PATENT DOCUMENTS

| | | | | |
|---|---|---|---|---|
| WO | WO-2015189283 A1 * | 12/2015 | | G01J 3/0218 |
| WO | WO-2018082136 A1 * | 5/2018 | | G01N 21/718 |

OTHER PUBLICATIONS

International Search Report and Written Opinion received for PCT/EP2020/068346, mailed Oct. 9, 2020.
International Preliminary Report on Patentability received for PCT/EP2020/068346, completed Sep. 24, 2021.
Beaumont, B., et al., "High efficiency conversion of laster energy and its application to optical power transmission," Proceedings of the Photovoltaic Specalists Conference, Oct. 1991, pp. 1503-1507.
Singh, N., et al., "InAlGaAs/InP-Based Laser Photovoltaic Converter at ~1070 nm," IEEE Electron Device Letters, vol. 37, No. 9, Sep. 2016, pp. 1154-1157.

* cited by examiner

DEVICE FOR PRODUCING GASEOUS $CO_2$ FROM CARBONATES FOR ISOTOPIC ANALYSIS ($\delta^{13}C$ AND $\delta^{18}O$) IN SITU, AND ASSOCIATED METHOD

BACKGROUND

The present invention relates to the preparation of gaseous samples from solid samples, in particular to the preparation of gaseous samples intended to be examined by isotopic analysis, for example by mass spectrometry or optical spectroscopy.

The present invention relates, in particular, to the preparation of gaseous samples from solid samples, mainly minerals containing carbon and/or oxygen.

More particularly, the present invention relates to the preparation of gaseous samples from rock samples containing carbonates intended to be examined by isotopic analysis of the carbon and/or oxygen.

The preparation of gaseous samples is known in the state of the prior art for the isotopic analysis of solid samples, in particular mineral samples, by chemical treatment. A ground fragment of the sample to be analyzed is chemically treated by dissolution in an acid, typically ortho-phosphoric acid, or by heating. This reaction produces carbon dioxide which is then injected into a mass spectrometer for isotopic analysis of the carbon and/or oxygen.

A drawback of this technique arises from the fact that it is necessary to take a fragment of the sample to be analyzed in the field and then to send it to the laboratory in order for it to be ground and prepared, in particular via treatments aimed at removing the organic material, before being chemically treated. These steps introduce a period of one to several weeks between the taking of the sample and the results, making the analysis time-consuming and costly in terms of consumables and human resources.

Another drawback of this technique is that it is sample-dependent. It requires the intervention of an expert in geology to develop the analysis protocol and the choice of the acid depending on the assessment that they will have made regarding the nature of the rock. It is common practice to carry out several treatments in view of the uncertainty related to the nature of the rock.

The preparation of gaseous samples is also known in the state of the art for the isotopic analysis of solid samples, in particular mineral samples, by laser ablation. The most widespread technique for carrying out this type of analysis is inductively coupled plasma mass spectrometry. This technique is implemented in a device comprising an ablation laser coupled to a mass spectrometer. The lasers used in this type of device are solid Q-switched, mainly Nd:YAG, lasers.

Like chemical treatment, a drawback of laser ablation arises from the fact that it is necessary to take a fragment of the sample to be analyzed in the field and to send it to the laboratory in order for it to be prepared for analysis, these techniques use apparatus the bulk and weight of which make it impossible to move it in situ.

An additional drawback that is inherent in the techniques for preparing gaseous samples for isotopic analysis by laser ablation is associated with the phenomenon of isotopic fractionation of the elements. This fractionation is due to recombinations and to variations of the recovery rate, which results in a modification of the isotopic ratio in the gaseous sample with respect to the actual isotopic ratio of the solid sample. This leads to skewed isotopic analysis results.

Another drawback of the techniques for preparing gaseous samples of the state of the art is that the efficiency of the isotope extraction reaction is not total for certain lasers. This lack of extraction efficiency is disadvantageous because it can induce an isotopic fractionation and distort the analyses.

Another drawback of the techniques for preparing gaseous samples of the state of the art is that they are matrix-dependent. The preparation is not identical for every solid sample but varies from one type of sample to another because of the matrix effects. This drawback necessitates the use of correction factors during the isotopic analysis of an element.

Another drawback of the techniques for preparing gaseous samples of the state of the art arises from the fact that a gas-phase chromatography step is carried out on the gaseous sample prior to the isotopic analysis.

Another drawback of the techniques for preparing gaseous samples of the state of the art is that they are sensitive to the organic pollution present on the surface or in the solid samples. The techniques of the state of the art therefore require the surface of the sample to be prepared before undertaking the preparation of the gaseous sample.

An aim of the invention is in particular to:
overcome at least one of the drawbacks of the techniques for preparing gaseous samples of the state of the art, and/or
to propose a preparation of gaseous samples that is impervious to the matrix effects, and/or
to propose a preparation of gaseous samples that does not require preparation, that is to say a cleaning step aimed at removing the organic surface pollution, and/or
to propose a preparation of gaseous samples that is impervious to the presence of organic carbon, and/or
to propose a preparation of gaseous samples the reaction efficiency of which is 100%, and/or
to propose a device for preparing gaseous samples that can be transported in situ, making in situ analysis possible, and/or
to propose a preparation of gaseous samples which makes it possible to analyse the gaseous sample directly without resorting to a gas-phase chromatography step before the isotopic analysis, and/or
to propose a preparation of gaseous samples which does not cause isotopic fractionation, or which at a minimum causes a negligible isotopic fractionation, and/or
to make a preparation of gaseous samples and/or an isotopic analysis possible directly in situ, for example on solid samples that are out of reach, at a drill head, or for example on solid samples that are situated in remote areas, and/or
to make an isotopic analysis possible that does not require the use of correction factors during the determination of the isotopy of an element, and in particular of carbon.

SUMMARY

To this end, a device for preparing a gaseous sample obtained from a solid sample is proposed, said device comprising:
a laser source arranged to emit a laser beam which is capable of generating calcination and/or combustion of a portion of the solid sample,
a means arranged to collect a gaseous sample of a gas emitted during the calcination and/or combustion of the portion of the solid sample; the device being characterized in that the laser beam has an irradiance less than 5 MW/cm² in a given impact zone on a surface of the sample, and in that it comprises an optical fibre for propagating the laser beam between the laser source and the given impact zone on the surface of the sample.

In the present application, when the term "device" is used on its own, it denotes the device for preparing a gaseous sample according to the invention.

According to the invention, the gaseous sample is intended to be examined by isotopic analysis.

The laser beam at the output of the laser source can have a power less than 500 W, preferably a power less than 100 W. The laser beam at the output of the laser source can have a power greater than 1 W.

Preferably, the laser beam has, in the given impact zone on the surface of the sample, an irradiance less than 1 MW/cm², preferably even less than 500 kW/cm², more preferably less than 100 kW/cm², even more preferably an irradiance less than 50 kW/cm², most preferably an irradiance less than 20 kW/cm².

The optical fibre makes it possible for the propagation of the laser beam between the laser source and the impact zone to be carried out in a confined manner so as to:

reach a sample situated far away from the laser source, and/or reach a sample out of reach of a user, and/or adapt, in real time, the path and the impact zone of the laser beam independently of the environment.

According to the invention, the laser beam:

makes it possible, in the impact zone, to heat the solid sample to a temperature above 600° C. and/or to a temperature below 1100° C., does not make it possible to extract material from the solid sample by laser ablation.

By "a laser beam which is capable of generating calcination and/or combustion of a portion of the solid sample" may be meant a laser beam which is capable of mainly or predominantly generating calcination and/or combustion of a portion of the solid sample.

By laser ablation is meant the extraction of material from the solid sample brought about directly by the interaction between the laser and the solid sample. This extraction is brought about directly by the laser, for example, by formation of a laser plasma, by atomization, by evaporation or by explosive evaporation or by a photochemical effect of the photoablative type or by mechanical shock.

A person skilled in the art will understand that by evaporation, generated by laser ablation, is meant the change from the solid state to the gaseous state of material from the solid sample (sublimation).

According to the invention, the laser source can be arranged to emit in:

continuous or quasi-continuous mode, and/or relaxed pulsed mode, and/or intermittent mode.

The laser source, operating in relaxed pulsed and/or intermittent mode for example, can be arranged to emit for a duration greater than 10 microseconds (µs), preferably greater than 50 µs, more preferably greater than 100 µs, even more preferably greater than 500 µs and most preferably greater than 1 second. Preferably, the laser source is arranged to emit in continuous or quasi-continuous mode.

According to the invention, the laser source is incapable of emitting in Q-switched mode.

According to the invention, the laser beam, in the impact zone, is not capable of causing a laser ablation, that is to say it is not capable of modifying the structure of the solid sample and/or of extracting material from the solid sample other than by the calcination reaction and/or the combustion which it induces in the given impact zone on the surface of the solid sample. The beam can be arranged so as to have an irradiance such that it causes heating of the given impact zone on the surface of the solid sample to a temperature close to or above 900° C.

According to the invention, an optical/electrical efficiency of the laser source can be greater than 30%.

Preferably, the optical/electrical efficiency of the laser source is greater than 40%. According to the invention, the laser source can operate at low voltage and at high current. By low voltage is meant a voltage value less than 50 volts and greater than or equal to 1 V. By high current is meant a current value greater than or equal to 1 ampere and less than 50 A.

The laser source can comprise a laser diode.

According to the invention:

the laser source can be a laser diode, or the laser source can be an optically pumped doped fibre.

The laser beam emitted by the laser diode can be injected into the optical fibre for propagating the laser beam between the laser source and the given impact zone on the surface of the sample.

The laser source can be arranged to emit a laser beam with a wavelength greater than 0.3 µm and/or less than 5 µm.

According to the invention, a diameter of a core of the optical fibre can have a value greater than 2 µm and/or less than 800 µm.

Preferably, the diameter of the core of the fibre can be greater than 5 µm. Preferably, the diameter of the core of the fibre can be comprised between 50 µm and 800 µm.

According to the invention, a numerical aperture of the optical fibre can be greater than 0.1 and/or less than 0.5.

The numerical aperture of the optical fibre can be, typically, 0.22.

The device according to the invention can comprise means for shaping and focusing the laser beam being arranged such that the device has a focal distance greater than 5 mm.

Preferably, the focal distance of the device is greater than 5 mm and/or less than 200 mm.

More preferably, the focal distance of the device is greater than 10 mm.

The optical fibre and the shaping and focusing means can be arranged such that the laser beam has a Rayleigh length greater than 0.5 mm and/or less than 10 mm.

Preferably, the laser beam has a Rayleigh length greater than 1.5 mm and/or less than 8 mm.

The device can be arranged such that a variation of a distance between the solid sample and an output of the means for shaping and focusing the laser beam of less than 2 mm causes a variation of a waist of the laser beam of less than 10%.

The device according to the invention can comprise a movement means arranged to move the laser beam and/or the impact zone relative to one another.

The optical beam can have an $M^2$ factor greater than 2 and/or less than 200. The $M^2$ factor gives information about the quality of the optical beam. Preferably, the optical beam has an $M^2$ factor greater than 5 and/or less than 150. More preferably, the optical beam has an $M^2$ factor greater than 20 and/or less than 150.

The device can comprise:

a light source arranged to illuminate at least the impact zone, an optical sensor arranged to image the illuminated impact zone and/or to measure one or more optical parameters of light reflected by the illuminated impact zone of the solid sample.

The light source can be arranged to emit in the visible. Preferably, the light source is arranged to emit a polychromatic light. More preferably, the light source is arranged to emit a white light.

The light source arranged to illuminate at least the impact zone can be the laser beam emitted by the laser source.

The laser beam emitted by the laser source can be used as the light source arranged to illuminate at least the impact zone, the laser beam in this case is incapable of generating calcination and/or combustion of the solid sample. Preferably, when the laser beam emitted by the laser source is used as the light source arranged to illuminate at least the impact zone, the laser beam has an irradiance, in the impact zone, less than 10 W/cm$^2$. Preferably, when the laser beam emitted by the laser source is used as the light source arranged to illuminate at least the impact zone, the laser beam at the output of the laser source has a power less than 1 W, preferably a power of several hundred milliwatts.

By way of non-limitative example, the optical parameter(s) of the light reflected by the impact zone of the solid sample can be a diffusion coefficient and/or a reflection coefficient and/or an absorption coefficient of the impact zone of the solid sample.

The device can comprise a processing unit arranged and/or configured and/or programmed to determine, from the optical parameter(s) measured by the optical sensor, a luminous flux to be applied to the impact zone.

The device can comprise a means arranged to deposit material on the impact zone of the solid sample, said material being arranged to initiate the calcination and/or combustion of the portion of the solid sample adjacent to the deposited material.

The device can comprise an enclosure arranged:
to cooperate with the means arranged to collect the gaseous sample,
such that the solid sample is arranged inside it, or
to be brought into direct contact with the surface of the solid sample.

The enclosure can be sealed or not.

The enclosure and/or the means arranged to collect the gas can comprise an opening.

The enclosure and/or the means arranged to collect the gas can be connected to a vacuum pump so as to generate a negative pressure in the enclosure and/or in the means arranged to collect the gas, respectively. The negative pressure which can be generated in the means arranged to collect the gas can generate a suction at the opening of the means arranged to collect the gas. The negative pressure which can be generated in the enclosure and/or the suction generated at the opening of the means arranged to collect the gas makes it possible to collect the gas emitted during the calcination and/or combustion.

The enclosure and/or the means arranged to collect the gas can comprise a sealing means arranged along their respective opening.

The enclosure and/or the means arranged to collect the gas can be sealed.

A primary or partial vacuum can be generated, by the vacuum pump connected to the enclosure and/or to the means arranged to collect the gas, in the enclosure and/or in the means arranged to collect the gas.

The device can comprise a gas inlet arranged so as to create an inert atmosphere in the enclosure and/or in the means arranged to collect the gas and/or in the impact zone of the solid sample. The gas injected through the gas inlet can be an inert gas such as, by way of non-limitative example, nitrogen or a noble gas such as helium or argon.

According to a first variant, the enclosure can comprise a removable part arranged to close the opening. The removable part can be arranged to close the opening of the enclosure in which the solid sample is arranged. The removable part can be arranged to seal the opening.

According to a second variant, the opening of the means arranged to collect the gas can be arranged to be brought into contact with the surface of the solid sample so as to close the means arranged to collect the gas. The opening of the means arranged to collect the gas can be arranged to be brought into contact with the surface of the sample so as to seal the enclosure.

Calcination is a reaction that does not require oxygen. In addition, according to the invention, when the device is arranged such that the enclosure and/or the means arranged to collect the gas and/or the impact zone of the solid sample is under a negative pressure or under vacuum or under an inert atmosphere, the laser beam causes only calcination of the solid sample. In this case, the preparation of the gaseous sample is impervious to the presence of organic pollution in or on the surface of the sample.

The device can comprise an optical element situated on a path of the laser beam at the output of the means for shaping and focusing the laser beam, said optical element being arranged to protect said means for shaping and focusing the laser beam.

The optical element can be an optical plate. The optical plate can comprise an anti-reflection coating, at the wavelength of the laser beam, on both of its two faces.

The optical element can be removable so as to be replaced. The optical element has the function of protecting the shaping and focusing means from the contamination generated by ambient dust and/or vapours produced during calcination and/or combustion.

According to the invention, a use of the device is also proposed for preparing a gaseous sample according to the invention, for the analysis
of carbon and/or oxygen isotopic compositions contained in carbonate rocks.

According to the invention, a portable device for the analysis of carbon and/or oxygen isotopic compositions contained in carbonate rocks is also proposed, said device for the analysis of isotopic compositions comprising:
the device for preparing a gaseous sample according to the invention,
an optical spectrometer or a mass spectrometer arranged to carry out isotopic analyses of elements contained in gaseous samples prepared by said device for preparing a gaseous sample.

The optical spectrometer arranged to carry out isotopic analyses can be an optical spectrometer with optical cavity (of the type used in Cavity Ring-Down Spectroscopy—CRDS). The optical spectrometer makes it possible, in particular, to carry out analyses in situ.

The mass spectrometer arranged to carry out isotopic analyses can be an isotope-ratio mass spectrometer (IRMS).

According to the invention, a method for preparing a gaseous sample obtained from a solid sample is also proposed, said method comprising:
emission, by a laser source, of a laser beam which is capable of generating calcination and/or combustion of a portion of the solid sample, collection, by a collection means, of a gaseous sample of a gas emitted during the calcination and/or combustion of the portion of the solid sample;

the method being characterized in that an irradiance of the laser beam emitted is less than 5 MW/cm² in a given impact zone on a surface of the sample, and in that it comprises propagation, by an optical fibre, of the laser beam between the laser source and the given impact zone on the surface of the sample.

According to the invention, a method of isotopic analysis is also proposed, comprising:

the method for preparing a gaseous sample obtained from a solid sample according to the invention, an isotopic analysis, by an optical spectrometer or a mass spectrometer, of elements contained in gaseous samples prepared by the device for preparing a gaseous sample.

BRIEF DESCRIPTION OF THE DRAWINGS

Other advantages and features of the invention will become apparent on reading the detailed description of implementations and embodiments that are in no way limitative, and from the following attached drawings.

DETAILED DESCRIPTION

As the embodiments described hereinafter are in no way limitative, variants of the invention can in particular be considered comprising only a selection of the characteristics described, in isolation from the other characteristics described (even if this selection is isolated within a phrase comprising these other characteristics), if this selection of characteristics is sufficient to confer a technical advantage or to differentiate the invention with respect to the state of the prior art. This selection comprises at least one, preferably functional, characteristic without structural details, or with only a part of the structural details if this part alone is sufficient to confer a technical advantage or to differentiate the invention with respect to the state of the prior art.

Figure 1:
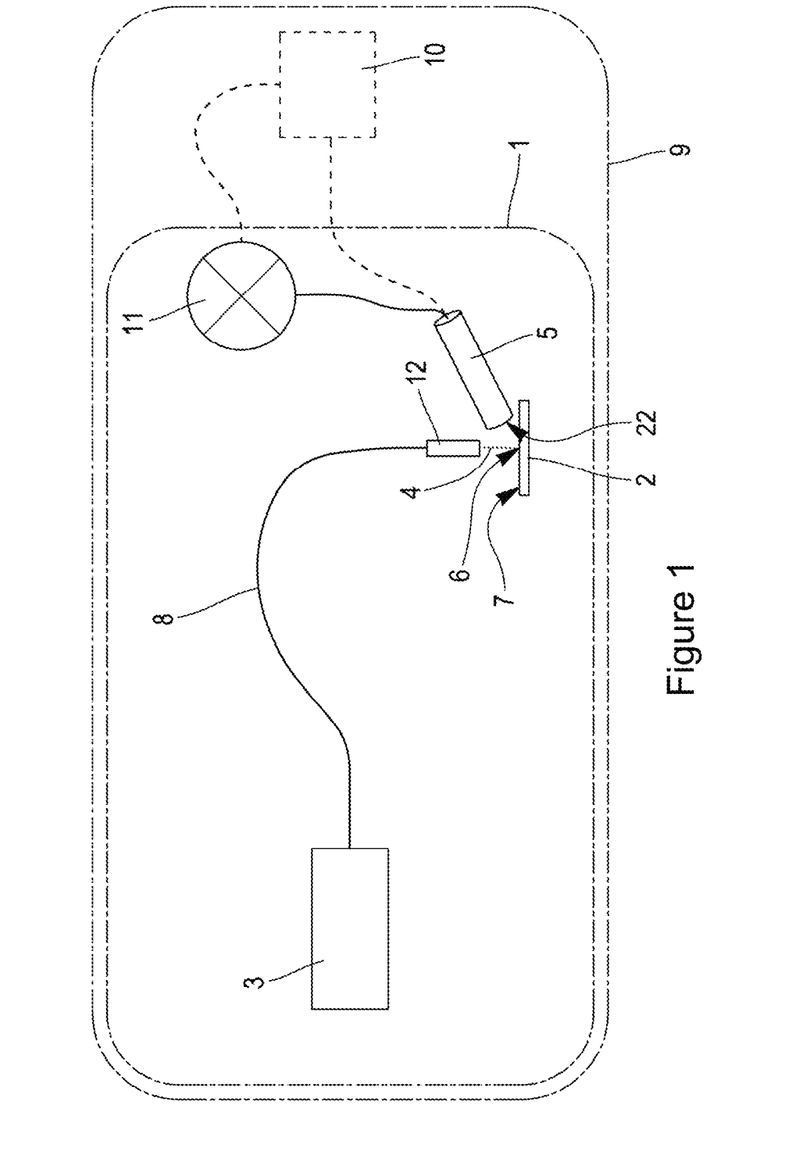
FIG. 1 illustrates a device for preparing a gaseous sample according to the invention and a device for isotopic analysis according to the invention.

A device for preparing a gaseous sample 1 obtained from a solid sample 2 is described with reference to FIG. 1. The device 1 comprises a laser source 3 arranged to emit a laser beam 4 which is capable of generating calcination and/or combustion of a portion of the solid sample 2. The device 1 also comprises a means arranged to collect a gaseous sample 5 of a gas emitted during the calcination and/or combustion of the portion of the solid sample 2. The laser beam 4 has an irradiance less than 5 MW/cm² in a given impact zone 6 on the surface 7 of the sample 2. The device 1 also comprises an optical fibre 8 for propagating the laser beam 4 between the laser source 3 and the given impact zone 6 on the surface 7 of the sample 2.

A device for collecting gases produced and for isotopic analysis 9 comprising the device for preparing a gaseous sample 1 and an optical spectrometer 10 arranged to carry out isotopic analyses of elements contained in the gaseous sample prepared by the device for preparing gaseous samples 1 is also described with reference to FIG. 1.

The gaseous sample prepared according to the invention is used directly, without any preparation, for the isotopic analysis. The gaseous sample prepared according to the invention is not subjected to a gas-phase chromatography step prior to the isotopic analysis.

A fibre laser diode 3 constitutes the laser source 3 and the optical fibre 8 of the device for preparing a gaseous sample 1. The fibre laser diode 3 is combined with a cooling system and a current controller. The use of optical fibre 8 is not possible with the laser sources used in the state of the art, in particular because the laser beams (their high power levels) emitted by the solid lasers damage the optical fibres 8 and because the optical fibres 8 made of silica do not allow the propagation of the laser beams (the wavelength of which is greater than 2 μm) emitted by the gas lasers.

Three fibre laser diodes 3 were selected for the tests. The fibre laser diodes 3 used have powers of 30 W for the first two and of 60 W for the third, respectively. The laser beams 4 emitted by the fibre laser diodes 3 have wavelengths of 808 for the first and 880 nm for the two others, respectively. The respective core diameters of the fibres of the fibre laser diodes 3 are 400 and 200 and 400 μm, respectively. The numerical aperture of the fibres of the fibre laser diodes 3 is 0.22. The calculated $M^2$ factor of the laser beam 4 is thus 80 for a fibre laser diode 3 emitting at 880 nm and having a core diameter of 200 μm. The laser beam 4 is emitted in continuous mode. The irradiance of the laser beams 4 of the fibre laser diodes 3 in the given impact zone 6 on the surface 7 of the sample 2 with a magnification telescope 2 and a focusing lens with a focal distance of 100 mm is approximately 10 to 20 kW/cm². As the laser beams 4 interact to a maximum depth of the solid sample 2 of 3 mm, the respective doses received by the sample 2 in one second are approximately 50 kJ/cm³ and 100 kJ/cm³. In the remainder of the description, the fibre laser diode 3 having a power of 30 W at 880 nm and a core diameter of 200 μm was used.

The irradiance of the fibre laser diode 3 is sufficient to heat the given impact zone 6 to a temperature close to 900° C. so as to initiate the calcination reaction but is insufficient to induce the phenomenon of laser ablation. As the ablation lasers are highly energetic, they generate reactive species which recombine and/or react with the isotopes of interest to be analyzed. The fibre laser diodes 3 used under the conditions according to the invention have the advantage of avoiding isotopic fractionation and therefore the loss of information.

The size of the laser beam 4 in the given impact zone 6 on the surface 7 of the sample 2 is of the order of several hundred micrometres. This makes it possible to carry out a localized analysis of the solid sample 2.

The solid sample 2 is a rock 2 containing carbonates. In contrast to the methods of the state of the art, the rocks are not processed, are not prepared and are not subjected to any surface treatment prior to the preparation of the gaseous sample.

The irradiation of the rock 2 using the laser beam 4 will cause calcination of the rock 2 which will predominantly give off carbon dioxide which will be collected in the form of a gaseous sample. In contrast to combustion, the calcination reaction is a reaction which, after having been initiated, is self-sustaining and does not require the presence of oxygen.

The isotopic analysis of the carbon and/or oxygen will be representative of the type of rock analyzed. Another advantage is the preparation almost solely on the calcination reaction, through the use of a fibre laser diode 3 under the conditions according to the invention, is obtaining a reaction efficiency which is 100% and recovering the maximum amount of carbon dioxide without losing information. The ablation lasers of the state of the art do not have an isotopic yield of 100%.

The ablation lasers also induce matrix effects which make the preparation of the gaseous sample dependent on the type of rock 2. Another advantage linked to the fact that the preparation of the gaseous sample is based almost solely on the calcination reaction is that the preparation is not matrix-dependent.

The device for preparing gaseous samples 1 comprises means for shaping and focusing 12 the laser beam 4 arranged so that the focal distance of the device for preparing a gaseous sample 1 is 100 mm. The shaping and focusing means 12 comprise, among others, achromats. The device for preparing gaseous samples 1 comprises a vacuum pump 11, for example a primary diaphragm or rotary vane vacuum pump 11 which is connected to the means for collecting gaseous samples 5 or to the optical spectrometer 10 which is itself connected to the means for collecting gaseous samples 5. The pump 11 makes it possible to create a negative pressure at the inlet 22 of the means for collecting a gaseous sample 5 making it possible to suck up a gas emitted during the calcination and/or combustion of the rock 2. The means for shaping and focusing 12 the laser beam 4 are also arranged so that the device for preparing gaseous samples 1 has a Rayleigh length approximately equal to 2 mm.

The Rayleigh length of the device for preparing gaseous samples 1 is such that a variation of the distance between the given impact zone 6 on the surface 7 of the rock 2 and the output 18 of the means for shaping and focusing 12 the laser beam 4 of less than 2 mm causes a variation of a waist of the laser beam of less than 10%.

The optical/electrical efficiency of the fibre laser diodes 3 is of the order of 40%, which makes it possible to obtain devices for preparing gaseous samples 1 that are battery-powered.

The fibre laser diodes 3 have a price which is much lower than that of solid or gas lasers.

The fact that the fibre laser diodes 3 operate at low voltage and high current, typically a maximum of 20 V and a maximum of 50 A, makes it possible to use compact electronics associated with the fibre laser diodes 3. The reduced bulk (of the order of 3 $dm^3$) of the assembly comprising the fibre laser diode 3, the Peltier device and the associated controllers makes it possible to transport the device for preparing gaseous samples 1 or the device for isotopic analysis 9 in situ. This makes it possible to prepare gaseous samples which are ready to be analyzed in situ or to carry out isotopic analyses directly in situ. The use of an optical fibre 8 makes it possible to analyse rocks in situ in confined areas and/or areas that are difficult to access and/or in areas not suitable for electronic equipment such as, by way of non-limitative example, at a drill head, in underground networks, in environments with water.

Figure 2:
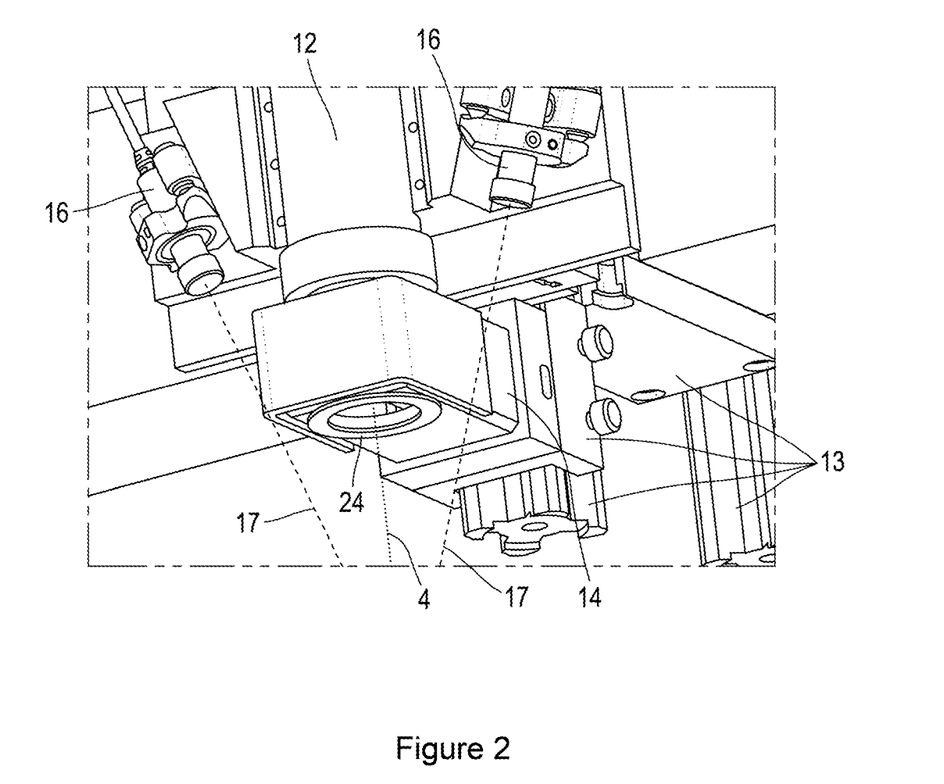
FIG. 2 illustrates an oblique view of the portion of the device for preparing a gaseous sample according to the invention situated at the output of the optical fibre of the device for isotopic analysis.
Figure 3:
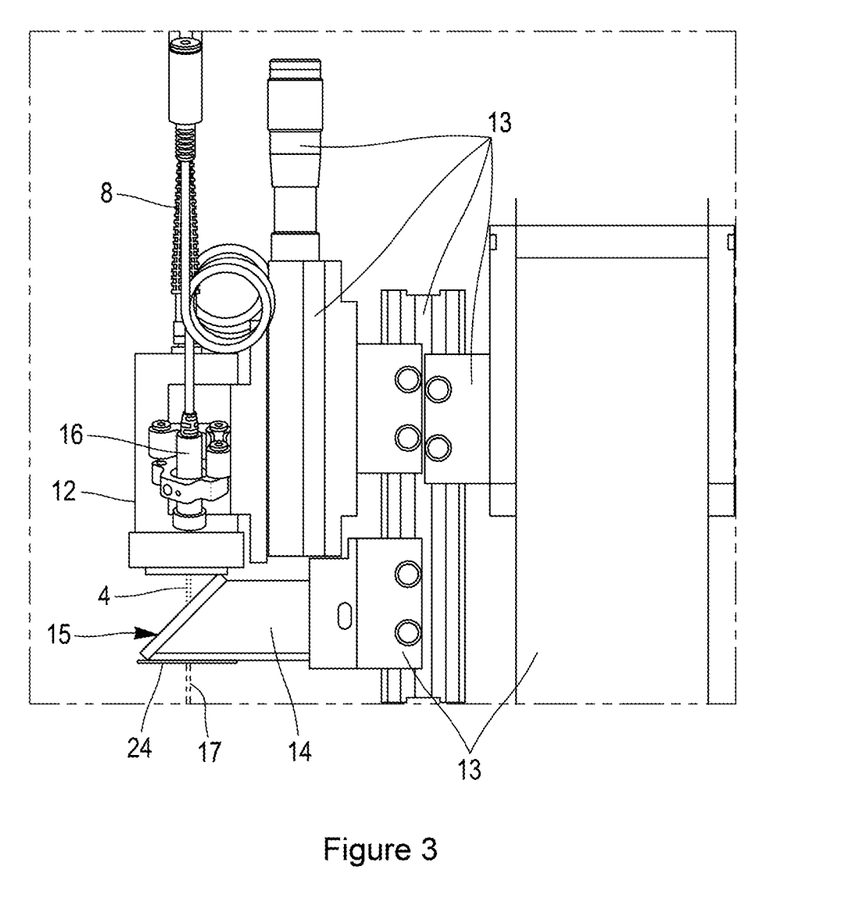
FIG. 3 illustrates a side view of the portion of the device for preparing a gaseous sample according to the invention situated at the output of the optical fibre of the device for isotopic analysis.

With reference to FIGS. 2 and 3, the device for preparing gaseous samples 1 comprises a guide table 13 arranged to move the laser beam 4 and/or the impact zone 6 relative to one another.

The device for preparing gaseous samples 1 comprises a white LED light source 24 arranged to illuminate at least the impact zone 6. The light source 24 is arranged in the form of a ring to produce an optimal illumination of the surface 7 of the rock 2. The device for preparing gaseous samples 1 also comprises a camera 14 arranged to image the illuminated impact zone. The device for preparing gaseous samples 1 comprises a two-way mirror 15 arranged to reflect a portion of the light reflected by the surface 7 of the rock 2 towards the camera 14.

The device for preparing gaseous samples 1 also comprises two red laser diodes 16 emitting aiming laser beams 17 which cross at a single point in the focal plane of the device for preparing gaseous samples 1.

Figure 4:
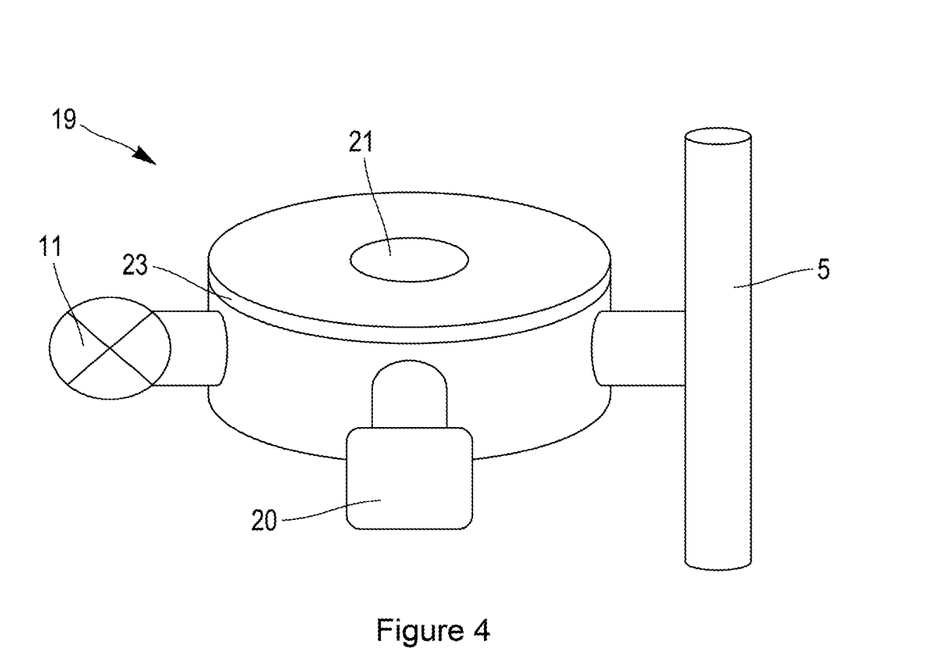
FIG. 4 illustrates an oblique view of an enclosure intended to be used together with the device for preparing a gaseous sample according to the invention.

With reference to FIG. 4, an enclosure 19 arranged so that the rock 2 is arranged inside it is proposed. The rock 2 is arranged in the enclosure 19 through an opening closed by a cover 23. The enclosure 19 is arranged to cooperate with the means arranged to collect the gaseous sample 5. A first opening of the enclosure 19 is connected to the pump 11 so as to be able to create a primary vacuum in the enclosure 19. A second opening of the enclosure 19 is connected to a vacuum gauge 20. The means arranged to collect the gaseous sample 5 is connected to a third opening of the enclosure 19. The upper face of the enclosure 19 comprises a window 21 made of glass through which, towards the rock 2 and/or from the rock 2, the light emitted by the white LED 24, the light reflected by the surface 6 of the rock 2, the laser beam 4 and the aiming laser beams 17 are propagated.

Tables 1 and 2 illustrate the results of isotopic analyses of the $^{13}C/^{12}C$ and $^{18}O/^{16}O$ ratios, respectively, measured by mass spectrometry on gaseous samples obtained from the rocks listed in Tables 1 and 2. These ratios are measured with respect to an International Atomic Energy Agency (IAEA) international standard (Pee Dee Belemnite (PDB)) and are given in the δ notation form in per mil. The results obtained by a commercial apparatus sold under the trade name "KIEL IV Carbonate Device" of the "Thermo Scientific" brand comprising a unit for preparing gaseous samples by chemical treatment according to the state of the art which is coupled to a mass spectrometer for the analysis of the prepared carbon dioxide are presented in Tables 1 and 2. The results obtained by the device for preparing gaseous samples 1 according to the invention coupled to the enclosure 19 are also presented in Tables 1 and 2; the gaseous samples thus prepared were analyzed by a commercial Delta V Plus mass spectrometer from "Thermo Scientific". The reproducibility of the preparation according to the invention when the impact zone 6 varies along the surface 7 of one and the same rock 2 is also entered in Tables 1 and 2.

TABLE 1

$\delta^{13}C/^{12}C$ isotopic ratio in per mil vs VPDB

| Name of the rock analyzed | Gaseous sample prepared by "KIEL IV Carbonate Device" | Gaseous sample prepared by the device according to the invention | Reproducibility of the measurements (1σ) |
|---|---|---|---|
| Calcite 2 | −0.25 | −0.635 | +/− 0.1 |
| Dolomite 2 | 3.31 | 4.06 | +/− 0.1 |
| Siderite 1 | −12.22 | −10.96 | +/− 0.1 |
| Malachite | −18.24 | −17.84 | +/− 0.1 |
| Siderite 2 | −12.27 | −11.73 | +/− 0.1 |
| Dolomite 1 | −12.22 | −10.66 | +/− 0.1 |
| Calcite 1 | 2.29 | 2.76 | +/− 0.1 |

TABLE 2

$\delta^{18}O/^{16}O$ isotopic ratio in per mil vs VPDB

| Rock analyzed | Gaseous sample prepared by "KIEL IV Carbonate Device" | Gaseous sample prepared by the device according to the invention | Reproducibility of the measurements (1σ) |
|---|---|---|---|
| Calcite 2 | −13.83 | −22.49 | +/− 0.2 |
| Dolomite 2 | −1.72 | −12.83 | +/− 0.2 |
| Siderite 1 | −14.57 | −22.03 | +/− 0.2 |
| Malachite | −3.3 | −14.02 | +/− 0.2 |
| Siderite 2 | −14.57 | −22.32 | +/− 0.2 |
| Dolomite 1 | −6.02 | −15.21 | +/− 0.2 |
| Calcite 1 | −3.38 | −13.38 | +/− 0.2 |

It should be noted that the variations between the measurements carried out in different impact zones 6 are substantially small. This demonstrates an excellent reproducibility of the preparation of gaseous samples according to the invention.

Figure 5:
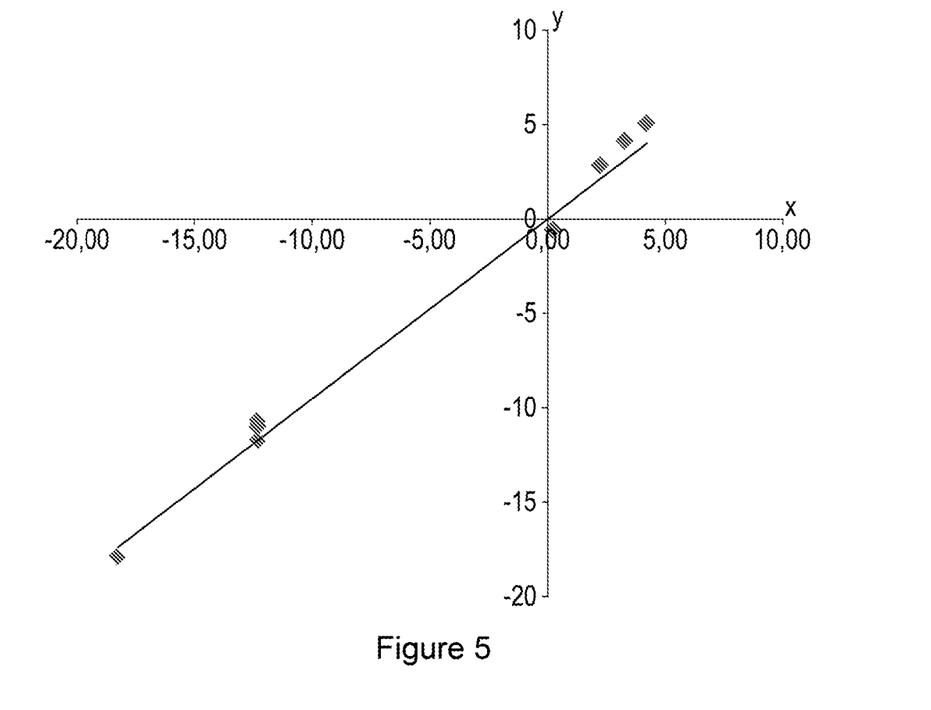
FIG. 5 is a graph representing the curve fitting carried out between the $^{13}C/^{12}C$ ratios measured on gaseous samples prepared by a commercial apparatus "KIEL IV Carbonate Device" from rocks of a batch of rocks, called panel, and the $^{13}C/^{12}C$ ratios measured on gaseous samples prepared by the device for preparing gaseous samples 1 according to the invention from rocks of the panel.
Figure 6:
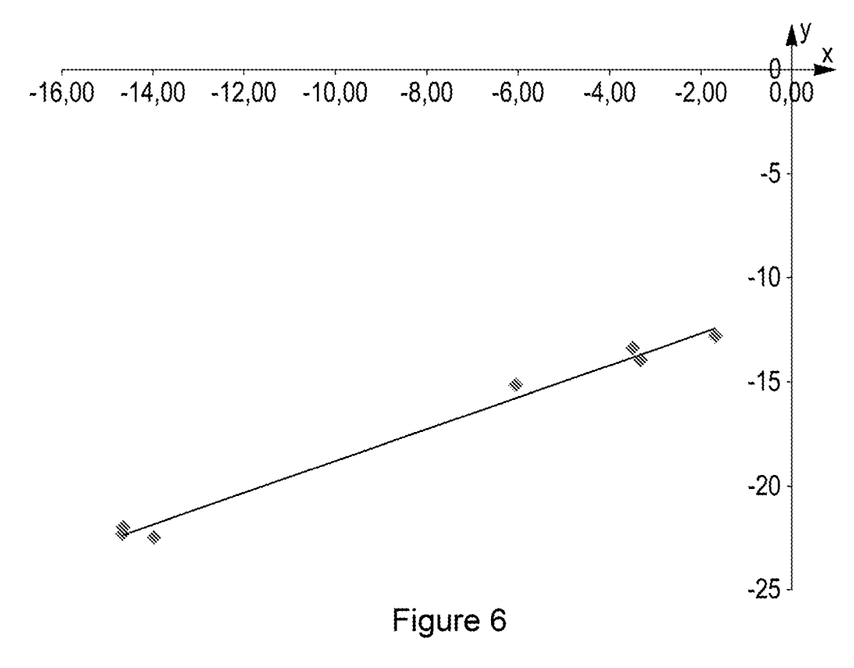
FIG. 6 is a graph representing the curve fitting carried out between the $^{18}O/^{16}O$ ratios measured on gaseous samples prepared by the commercial apparatus "KIEL IV Carbonate Device" from rocks of the panel and the $^{18}O/^{16}O$ ratios measured on gaseous samples prepared by the device for preparing gaseous samples 1 according to the invention from rocks of the panel.

FIGS. 5 and 6 illustrate the curve fitting carried out between the $^{13}C/^{12}C$ and $^{18}O/^{16}O$ ratios measured by the commercial apparatus "KIEL IV Carbonate Device" on the different rocks of the panel and the $^{13}C/^{12}C$ and $^{18}O/^{16}O$ ratios measured on the gaseous samples prepared by the device for preparing gaseous samples 1 according to the invention from the different rocks of the panel, respectively. The values of the isotopic ratios measured are provided in Tables 1 and 2. The abscissa, denoted x, shows the $^{13}C/^{12}C$ and $^{18}O/^{16}O$ ratios measured by the commercial apparatus "KIEL IV Carbonate Device" and the ordinate, denoted y, shows the $^{13}C/^{12}C$ and $^{18}O/^{16}O$ ratios measured on the gaseous samples prepared by the device for preparing gaseous samples 1 according to the invention. Each point illustrates the values of the $^{13}C/^{12}C$ and $^{18}O/^{16}O$ ratios measured on a particular sample as listed in Tables 1 and 2. The solid straight line corresponds to the curve fitting carried out by linear regression between the different points.

The correlation coefficient between the $^{13}C/^{12}C$ ratio measured by the commercial apparatus "KIEL IV Carbonate Device" and the $^{13}C/^{12}C$ ratio measured on
the gaseous sample prepared by the device for preparing gaseous samples 1 is 0.994. The correlation coefficient between the $^{18}O/^{16}O$ ratio measured by the commercial apparatus "KIEL IV Carbonate Device" and the $^{18}O/^{16}O$ ratio measured on the gaseous sample prepared by the device for preparing gaseous samples 1 is 0.989.

The very good correlation coefficients observed demonstrate that the preparation of the gaseous samples according to the invention is equivalent to that carried out by the commercial apparatus "KIEL IV Carbonate Device", which is currently considered to be one of the reference pieces of apparatus for isotopic analysis of carbonate rocks.

Of course, the invention is not limited to the examples that have just been described, and numerous modifications may be made to these examples without exceeding the scope of the invention.

Thus, in the variants that can be combined together of the embodiments described above:
  the laser source 3 is an optically pumped doped fibre 3, and/or
  the laser beam 4 is emitted in relaxed pulsed and/or intermittent mode; in particular in order to limit the quantity of gas produced during calcination and/or combustion, and/or
  the cooling system associated with the laser source 3 is:
  a Peltier module, or
  a conductive cooling system, and/or
  the two-way mirror 15 is a high-pass filter which is transparent at 45° incidence to infrared wavelengths and which is reflective for visible wavelengths which are captured by the camera 14, and/or
  the device for preparing gaseous samples 1 comprises a low-pass filter (of the KG3 type, not shown) stuck onto an objective (not shown) of the camera 14 makes it possible to eliminate the infrared radiation of the fibre laser diode 3 that is backscattered and reflected by the rock 2 during the preparation of the gaseous sample, and/or
  the device for isotopic analysis 9 comprises a mass spectrometer 10 arranged to carry out isotopic analyses of elements contained in a
  gaseous sample prepared by the device for preparing a gaseous sample 1, and/or
  the device for preparing gaseous samples 1 comprises an optical element situated on a path of the laser beam 4 at the outlet 18 of the means for shaping and focusing 12 the laser beam 4, the optical element is arranged to protect the means for shaping and focusing 12 the laser beam 4, and/or
  the device for preparing gaseous samples 1 comprises a means arranged to deposit material on the impact zone 6 of the solid sample 2, the material being arranged to initiate the calcination and/or combustion of the portion of the solid sample 2 adjacent to the deposited material; this is particularly useful when the solid sample 2 has a low absorption coefficient vis-à-vis the laser beam 4, and/or
  the optical sensor 14 of the device for preparing gaseous samples 1 is arranged to measure one or more optical parameters of the light reflected by the surface 7 of the solid sample 2 illuminated by the laser source 3 or by a secondary light source or by the white LED source 24, and/or
  the device for preparing gaseous samples 1 comprises a processing unit arranged and/or configured and/or programmed to determine, from the optical parameter(s) measured by the optical sensor 14, a luminous flux to be applied to the impact zone 6, and/or
  the material deposited on the impact zone of the solid sample 2 comprises iron oxides, and/or
  the first opening of the enclosure is connected to an inert gas source 11, by way of non-limitative example nitrogen, so as to create an inert atmosphere in the enclosure 19 by sweeping the enclosure 19 with a stream of nitrogen, and/or a stream of inert gas can be injected, by means of a gas inlet, in the impact zone 6 of the solid sample 2 so as to sweep the zone with a stream of inert gas during the preparation; this has the effect of making the preparation of a gaseous sample impervious to the presence of organic carbon in or on the surface 7 of the solid sample 2, and/or the inlet 22 of the means arranged to collect the gaseous sample 5 is brought into contact with the surface 7 of the rock 2 so as to close the means arranged to collect the gaseous sample 5; this has the effect of making the preparation of a gaseous sample impervious to the presence of organic carbon in or on the surface 7 of the solid sample 2, and/or a circumference of the inlet 22 of the means arranged to collect the gaseous sample 5 comprises a gasket arranged to be brought to rest directly against the surface 7 of the rock 2 so as to seal the enclosure 19.

In addition, the various characteristics, forms, variants and embodiments of the invention can be combined together in various combinations, to the extent that they are not incompatible or mutually exclusive.

The invention claimed is:

1. A device for preparing a gaseous sample obtained from a solid sample, said device comprising:
   a laser source arranged to emit a laser beam generating calcination and/or combustion of a portion of the solid sample and said laser beam not causing a laser ablation;
   a means arranged to collect a gaseous sample of a gas emitted during the calcination and/or combustion of the portion of the solid sample;
   the laser beam has an irradiance less than 5 MW/cm2 in a given impact zone on a surface of the sample; and
   an optical fibre for propagating the laser beam between the laser source and the given impact zone on the surface of the sample.

2. The device according to claim 1, wherein an optical/electrical efficiency of the laser source is greater than 30%.

3. The device according to claim 1, wherein the laser source comprises a laser diode.

4. The device according claim 3, wherein:
   the laser source is a laser diode, or
   the laser source is an optically pumped doped fibre.

5. The device according to claim 1, wherein the laser source is arranged to emit a laser beam with a wavelength greater than 0.3 µm and/or less than 5 µm.

6. The device according to claim 1, wherein a diameter of a core of the optical fibre has a value greater than 2 µm and/or less than 800 µm.

7. The device according to claim 1, wherein a numerical aperture of the optical fibre is greater than 0.1 and/or less than 0.5.

8. The device according claim 1, comprising means for shaping and focusing the laser beam being arranged such that the device has a focal distance greater than 5 mm.

9. The device according to claim 8, wherein the laser source, the optical fibre and the shaping and focusing means are arranged such that the laser beam has a Rayleigh length greater than 0.5 mm and/or less than 10 mm.

10. The device according to claim 1, comprising a movement means arranged to move the laser beam and/or the impact zone relative to one another.

11. The device according to claim 1, wherein the optical beam has an M2 factor greater than 2 and/or less than 200.

12. The device according claim 1, comprising:
    a light source arranged to illuminate at least the impact zone; and
    an optical sensor arranged to image the illuminated impact zone and/or to measure one or more optical parameters of light reflected by the illuminated impact zone of the solid sample.

13. The device according to claim 12, comprising a processing unit arranged and/or configured and/or programmed to determine, from the optical parameter(s) measured by the optical sensor, a luminous flux to be applied to the impact zone.

14. The device according to claim 1, comprising a means arranged to deposit material on the impact zone of the solid sample, said material being arranged to initiate the calcination and/or combustion of the portion of the solid sample adjacent to the deposited material.

15. The device according to claim 1, comprising an enclosure arranged:
    to cooperate with the means arranged to collect the gaseous sample,
    such that the solid sample is arranged inside it, or
    to be brought into direct contact with the surface of the solid sample.

16. The device according to claim 1, comprising an optical element situated on a path of the laser beam at the output of the means for shaping and focusing the laser beam, said optical element being arranged to protect said means for shaping and focusing the laser beam.

17. A portable device for the analysis of carbon and/or oxygen isotopic compositions contained in carbonate rocks, said device for the analysis of isotopic compositions comprising:
    the device for preparing a gaseous sample according to claim 1; and
    an optical spectrometer or a mass spectrometer arranged to carry out isotopic analyses of elements contained in gaseous samples prepared by said device for preparing a gaseous sample.

18. A use of the device for preparing a gaseous sample according to claim 1, for the analysis of carbon and/or oxygen isotopic compositions contained in carbonate rocks.

19. A method for preparing a gaseous sample obtained from a solid sample, said method comprising:
    emission, by a laser source, of a laser beam generating calcination and/or combustion of a portion of the solid sample and said laser beam not causing a laser ablation;
    collection, by a collection means, of a gaseous sample of a gas emitted during the calcination and/or combustion of the portion of the solid sample;
    an irradiance of the laser beam emitted is less than 5 MW/cm2 in a given impact zone on a surface of the sample; and
    propagation, by an optical fibre, of the laser beam between the laser source and the given impact zone on the surface of the sample.

* * * * *